(12) United States Patent
Rezach et al.

(10) Patent No.: US 10,687,862 B2
(45) Date of Patent: Jun. 23, 2020

(54) SPINAL IMPLANT CONNECTOR AND METHODS

(71) Applicant: Warsaw Orthopedic, Inc., Warsaw, IN (US)

(72) Inventors: William Alan Rezach, Covington, TN (US); Molly K. Rice, Memphis, TN (US); Leigh Anna Folger, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 35 days.

(21) Appl. No.: 15/940,180

(22) Filed: Mar. 29, 2018

(65) Prior Publication Data

US 2019/0298422 A1  Oct. 3, 2019

(51) Int. Cl.
   *A61B 17/70* (2006.01)
   *A61B 17/68* (2006.01)
   *A61B 17/86* (2006.01)

(52) U.S. Cl.
   CPC ...... *A61B 17/7052* (2013.01); *A61B 17/7002* (2013.01); *A61B 17/705* (2013.01); *A61B 17/8695* (2013.01); *A61B 2017/681* (2013.01)

(58) Field of Classification Search
   CPC ............ A61B 17/7052; A61B 17/7002; A61B 17/705; A61B 17/8695; A61B 2017/681
   See application file for complete search history.

(56) References Cited

U.S. PATENT DOCUMENTS

| | | | |
|---|---|---|---|
| 5,643,263 A | 7/1997 | Simonson | |
| 5,885,285 A | 3/1999 | Simonson | |
| 6,562,038 B1 | 5/2003 | Morrison | |
| 6,579,292 B2 | 6/2003 | Taylor | |
| 6,872,209 B2 | 3/2005 | Morrison | |
| 7,066,939 B2 | 6/2006 | Taylor | |
| 7,261,715 B2* | 8/2007 | Rezach | A61B 17/7037 606/60 |
| 8,097,023 B2 | 1/2012 | Cline, Jr. et al. | |
| 2005/0228378 A1* | 10/2005 | Kalfas | A61B 17/705 606/252 |
| 2007/0162008 A1* | 7/2007 | Cline, Jr. | A61B 17/7037 606/60 |
| 2007/0293861 A1 | 12/2007 | Rezach et al. | |
| 2010/0160971 A1* | 6/2010 | Glerum | A61B 17/7037 606/278 |
| 2011/0196425 A1 | 8/2011 | Rezach et al. | |

(Continued)

OTHER PUBLICATIONS

International Search Report and Written Opinion for PCT/US2019/023995, the counterpart application dated Jul. 8, 2019, 12 pages.

*Primary Examiner* — Tessa M Matthews

(57) ABSTRACT

A connector includes a first receiver that defines an implant cavity and includes a mating surface. A second receiver attachable with the first receiver via a flexible element, the second receiver defines an implant cavity and includes a mating surface engageable with the mating surface of the first receiver to fix relative orientation of the receivers. A biasing element is disposed adjacent the mating surfaces to space the mating surfaces such that the first receiver is movable relative to the second receiver in operation of the connector. Systems, surgical instruments, implants, spinal constructs and methods are disclosed.

20 Claims, 13 Drawing Sheets

(56) References Cited

U.S. PATENT DOCUMENTS

2012/0004659 A1\* 1/2012 Miller ................ A61B 17/6466
 606/54
2012/0029571 A1\* 2/2012 Schwab ............... A61B 17/705
 606/278
2012/0179205 A1 7/2012 Miller \* cited by examiner

SPINAL IMPLANT CONNECTOR AND METHODS

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as kyphosis, scoliosis and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. In some cases, the rods are interconnected as part of a surgical treatment. This disclosure describes an improvement over these prior technologies.

SUMMARY

In one embodiment, a connector is provided. The connector includes a first receiver that defines an implant cavity and includes a mating surface. A second receiver attachable with the first receiver via a flexible element, the second receiver defines an implant cavity and includes a mating surface engageable with the mating surface of the first receiver to fix relative orientation of the receivers. A biasing element is disposed adjacent the mating surfaces to space the mating surfaces such that the first receiver is movable relative to the second receiver in operation of the connector. In some embodiments, systems, surgical instruments, spinal constructs, implants and methods are disclosed.

In one embodiment, a method of assembling a spinal implant is provided. The method comprises the steps of: aligning a surface of a first receiver with a surface of a second receiver to define a passageway; introducing a flexible element through one of the receivers to adjacent the passageway; and positioning the flexible element in the passageway to attach the first receiver with the second receiver.

In one embodiment, a method of treating a spine is provided. The method comprises the steps of: disposing a first spinal rod with a first receiver of a spinal implant, the first receiver having a mating surface and the spinal implant including a second receiver attachable with the first receiver via a flexible element, the second receiver having a mating surface and a biasing element disposed adjacent the mating surfaces to space the mating surfaces such that the first receiver is movable relative to the second receiver; disposing a second spinal rod with the second receiver; and engaging the mating surfaces to fix relative orientation of the receivers.

BRIEF DESCRIPTION OF THE DRAWINGS

The present disclosure will become more readily apparent from the specific description accompanied by the following drawings, in which:

FIG. 4 is a side view of a second receiver of the system shown in

FIG. 1;

DETAILED DESCRIPTION

Figure 1:
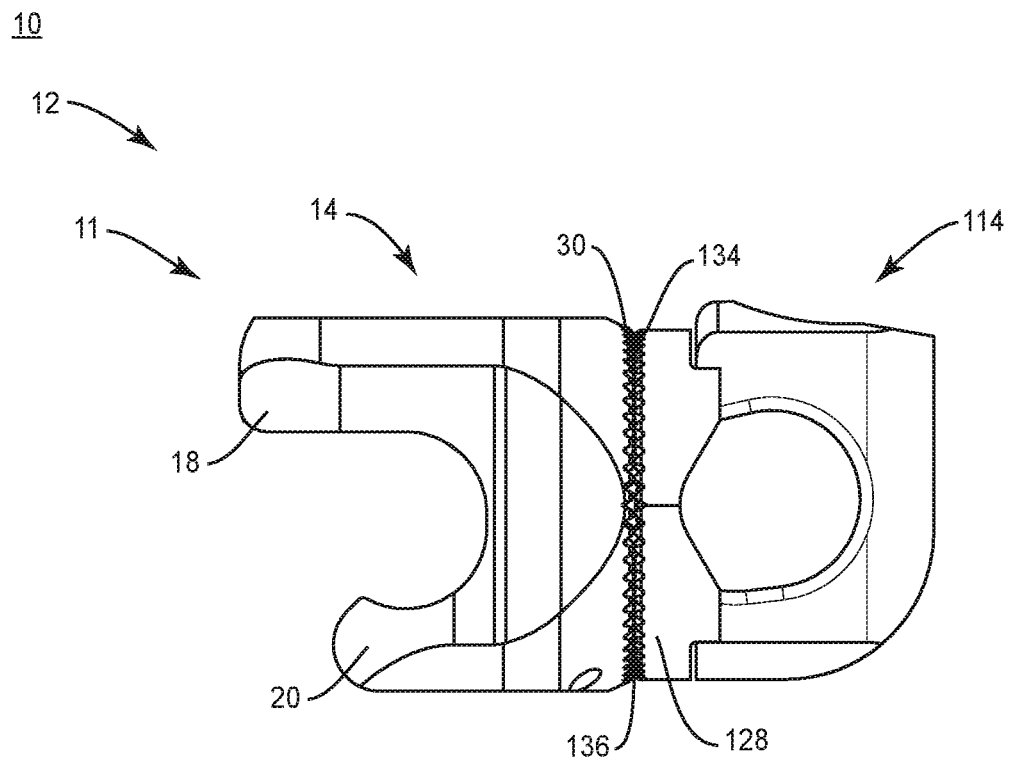
FIG. 1 is a side view of components of one embodiment of a system in accordance with the principles of the present disclosure.
Figure 2:
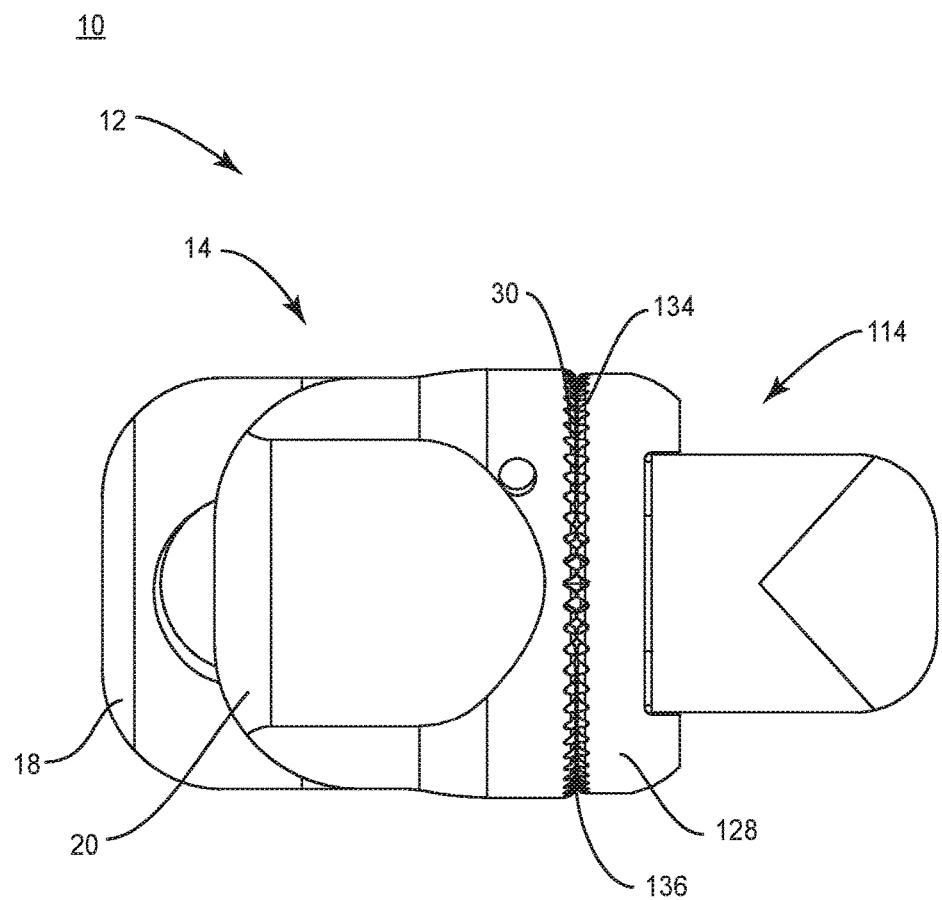
FIG. 2 is a bottom view of the components shown in FIG. 1.

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the present surgical system includes a spinal construct comprising a connector. In some embodiments, the present surgical system includes a spinal construct comprising a variable angle domino connector. In some embodiments, the present surgical system includes a spinal construct comprising one or more revision minimally invasive surgical connectors. In some embodiments, the present surgical system includes a spinal construct that can be employed with a method for treating a spine with a plurality of spinal rods, which can be used to hold a spine until fusion occurs. In some embodiments, the present surgical system includes a spinal construct that can be employed with a method for treating a spine, which includes a pedicle subtraction osteotomy, a three column osteotomy, a transforaminal lumbar interbody fusion (TLIF) and/or long constructs in heavy patients.

In some embodiments, the present surgical system includes a spinal construct comprising a rod-to-rod connector used to connect two rods in a multi-rod construct or for extension of an existing construct. In some embodiments, opposing sides of the connector move independently and allow rods of different contours to be connected without additional manipulation of the rods. In some embodiments, the connector includes an open component. In some embodiments, the connector includes a closed component. In some embodiments, the connector includes a splined washer. In some embodiments, the connector includes an O-ring. In some embodiments, the connector includes an assembly wire. In some embodiments, the connector includes articulating components configured to reduce the amount of rod bending for attaching spinal rods with the connector. In some embodiments, this configuration allows the connector to be employed with multi-rod spinal constructs having spinal rods with different contours.

In some embodiments, the present surgical system includes a spinal construct comprising a rod-to-rod connector that is employed with a method such that when a user locks a set screw onto a spinal rod disposed with the closed component, the splined washer is forced toward the splines on the open component. In some embodiments, this step also compresses the O-ring and engages the splines to lock an orientation of the closed component in relation to the open component while simultaneously locking the spinal rod disposed with the closed component in a selected orientation. In some embodiments, a spinal rod disposed with the open component rod is then locked down with a separate set screw. In some embodiments, the connector can include an open component and/or a closed component that can accommodate one or a plurality of spinal rod sizes and/or diameters. In some embodiments, the rods may not include a circular cross section.

In some embodiments, the present surgical system includes a spinal construct comprising a rod-to-rod connector and includes a method of assembling the connector. In some embodiments, the method of assembly includes the step of driving or otherwise delivering an assembly wire through an assembly channel of a connector component. In some embodiments, the channel is created by the alignment of an open component and a closed component. In some embodiments, the assembly wire is disposed with the connector to resist and/or prevent the connector components from moving apart while allowing the components to rotate about a common axis. In some embodiments, a length and/or diameter of the wire is selected for disposal with the components to provide a slidable relative rotation between the connector components. In some embodiments, a diameter of the wire is selected to not occupy the entire space and/or diameter of the wire channel. In some embodiments, this configuration limits tolerance and/or toggle between the connector components. In some embodiments, a length of the wire is selected so that when the wire is pushed completely through an entry channel of a connector component, for example, the open component, and then into the assembly channel, the wire creates a generally C-shape. In some embodiments, the wire is biased within the assembly channel to expand outwardly such that the wire contacts only an inner surface of the component that defines the female aspect of the assembly channel. In some embodiments, this configuration limits contact of the wire to the component with the female aspect of the assembly channel to effectively limit the amount of frictional engagement of the wire with the connector components during relative rotation of the components. In some embodiments, the C-shape configuration of the wire and position of the entry channel in relation to the assembly channel eliminates additional assembly steps, for example, staking, for maintaining the wire in the assembly channel. In some embodiments, the wire is disposed with the assembly channel such that the wire is disposed tangent to an inner wall that defines the assembly channel and is not disposed tangent to an outer wall that defines the assembly channel.

In some embodiments, the present surgical system includes a spinal construct comprising a rod-to-rod connector having a silicone O-ring configured to maintain spacing or a gap between the splines of the washer and the splines of the open component until final tightening of the closed component. In some embodiments, maintaining the spacing or gap between the splines allows articulation of the components. In some embodiments, a set screw of the closed component is locked down such that a spinal rod disposed with the closed component pushes the washer into the O-ring. The O-ring is compressed which allows the splines to engage.

In some embodiments, the connector includes a closed component having a spinal rod channel with a tear-drop cross section configuration. In some embodiments, the spinal rod channel has an angled cross section oriented toward the mating washer. In some embodiments, this configuration creates a larger opening for insertion of a spinal rod. In some embodiments, this configuration includes an angle and positioning of the set screw relative to a lateral half of the spinal rod that facilitates driving the rod down a ramp of the spinal rod channel to push against the washer to lock the connector components in a selected in position.

In some embodiments, the present surgical system includes a spinal construct comprising bone screws and a spinal rod connector. In some embodiments, the present surgical system includes a spinal construct that can be employed with a method for treating a spine, which includes attaching a secondary rod to an existing spinal rod. In some embodiments, the present surgical system includes a spinal construct that can be employed with a method for treating a spine, which includes revision of a fractured rod. In some embodiments, a new rod can be installed into the connectors bridging the fracture of the rod regardless of the proximity of the existing pedicle screws. In some embodiments, the present surgical system includes a spinal construct that can be employed with a method for treating a spine, which includes connecting a second rod to a construct.

In some embodiments, the spinal construct includes a spline assembly that allows for rotation, which may include rod angulation, for example in a coronal orientation, before the setscrew is tightened and interdigitate when the setscrew is tightened to lock the spinal construct. In some embodiments, the spinal construct includes a spline assembly that allows for rotation, which may include rod angulation, for example in a sagittal orientation, before the setscrew is tightened and interdigitate when the setscrew is tightened to lock the spinal construct. In some embodiments, the spinal construct includes a rod receiver with fixed coronal angle offset. In some embodiments, the spinal construct includes a rod receiver with fixed sagittal angle offset. In some embodiments, the spinal construct includes a revision connector configured to attach to one or more existing spinal constructs implanted with a body. In some embodiments, the spinal construct can be employed in a revision surgery to extend an existing screw and rod construct. In some embodiments, the spinal construct can be employed in a revision surgery to connect an existing spinal construct and extend the existing spinal construct to span one or more spinal levels.

In some embodiments, the present surgical system includes a spinal construct that can be employed in a revision surgery to connect to an existing rod implanted with a body. In some embodiments, the spinal construct and the existing spinal construct comprise an extension. In some embodiments, the present surgical system includes a spinal construct that can be employed in a revision surgery to connect to an existing bone screw and rod construct through a minimally invasive approach. In some embodiments, the present surgical system includes a spinal construct having an adjustable rod geometry such that the rod is loaded to the connector after delivery of the connector to a surgical site.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are disclosed. Reference is made to the exemplary embodiments of the present disclosure, which are illustrated in the accompanying figures. Turning to FIGS. 1-13, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of spinal implant system 10 are configured for engagement with existing constructs, which may include fastener implants and/or spinal rod implants attached with vertebrae, in a revision surgery to manipulate tissue and/or correct a spinal disorder, as described herein. In some embodiments, one or more of the components of spinal implant system 10 can be employed in a revision surgery to connect an existing spinal construct and extend, revise or repair the existing spinal construct to span one or more spinal levels. Spinal implant system 10 comprises a spinal construct 11. In some embodiments, one or more components of spinal construct 11 are configured to extend an existing spinal rod implant with or without removing the existing rod implant. In some embodiments, existing spinal constructs may include one or more implants connected or fixed with tissue in a prior or different surgical procedure, separate in time and/or over a duration of time in the same surgical procedure.

Spinal construct 11 includes a connector 12. Connector 12 is configured as a variable-angle connector 12. In some embodiments, connector 12 is a rod-to-rod connector having receivers that rotate independent of each other to facilitate connecting rods of varying contours with tissue, such as, for example, vertebrae.

Figure 3:
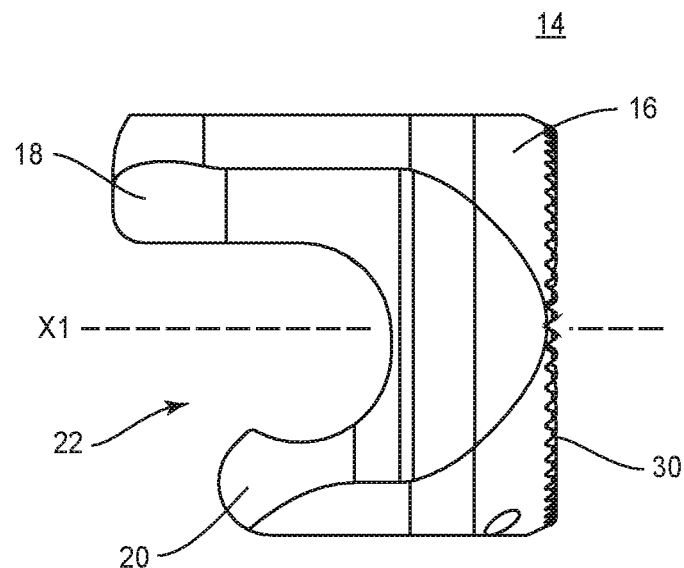
FIG. 3 is a side view of a first receiver of the system shown in FIG. 1.

Connector 12 includes a receiver 14 and a receiver 114, as described herein. Receiver 14 includes a body 16 that extends along an axis X1. Receiver 14 includes a pair of spaced apart arms 18, 20 that define an implant cavity, such as, for example, a passageway 22. In some embodiments, passageway 22 is configured for disposal of a spinal implant, such as, for example, a spinal rod 200 to extend and/or revise an existing spinal construct, as described herein. Passageway 22 is configured for side loading of spinal rod 200. In some embodiments, passageway 22 can be positioned for alternate loading orientations, such as, for example, top, lateral and/or positions disposed transverse to axis X1. Arms 18, 20 each extend parallel to an axis X1, as shown in FIG. 3. In some embodiments, arm 18 and/or arm 20 may be disposed at alternate orientations, relative to axis X1, such as, for example, transverse, perpendicular and/or other angular orientations such as acute or obtuse, coaxial and/or may be offset or staggered.

Figure 13:
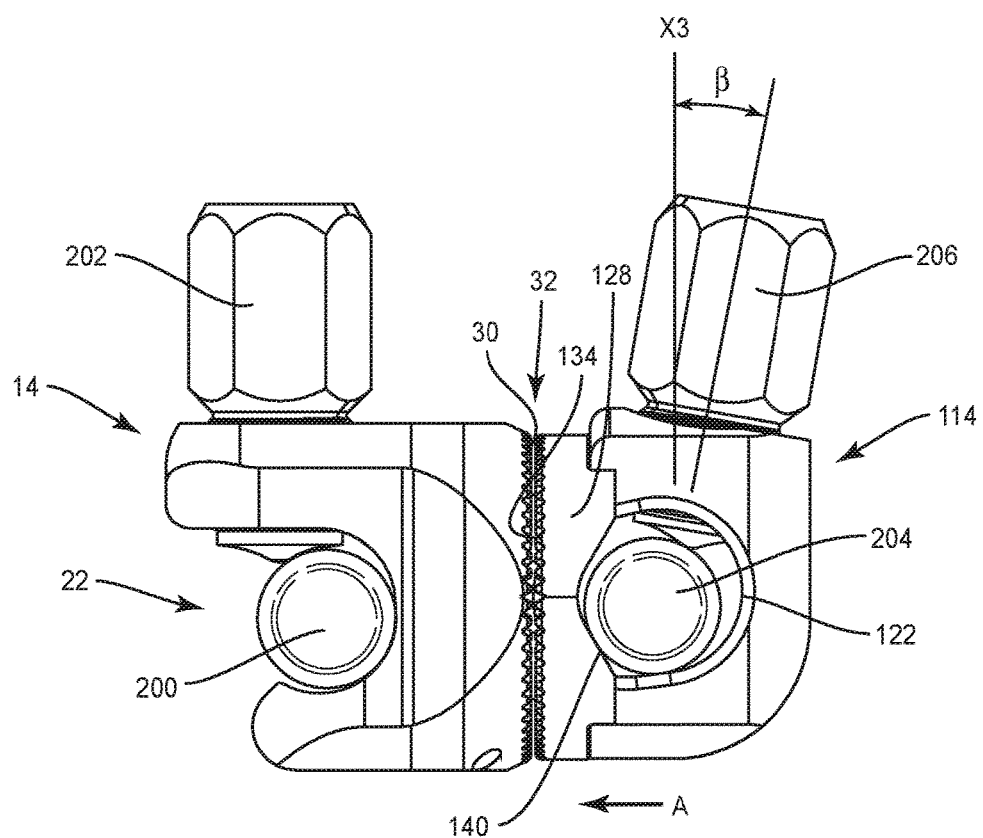
FIG. 13 is a side view of components of one embodiment of a system in accordance with the principles of the present disclosure.

Passageway 22 in various embodiments is substantially U-shaped. In some embodiments, all or only a portion of passageway 22 may have alternate cross section configurations, such as, for example, closed, V-shaped, W-shaped, oval, oblong triangular, square, polygonal, irregular, uniform, non-uniform, offset, staggered, and/or tapered. Body 16 includes an inner surface 24. A portion of surface 24 includes a thread form 26 located with arm 18. Thread form 26 is configured for engagement with a coupling member, such as, for example, a set screw 202, to retain rod 200 within passageway 22, as shown in FIG. 13. In some embodiments, surface 24 may be disposed with a set screw in alternate fixation configurations, such as, for example, friction fit, pressure fit, locking protrusion/recess, locking keyway and/or adhesive. In some embodiments, all or only a portion of surface 24 may have alternate surface configurations to enhance engagement with a spinal rod and/or a set screw such as, for example, rough, arcuate, undulating, mesh, porous, semi-porous, dimpled and/or textured. Set screw 202 is configured for engagement with rod 200 to facilitate fixation and/or locking of rod 200 with receiver 14. Set screw 202 is disposable with receiver 14 between a non-locking orientation, such that rod 200 is translatable relative to connector 12 and a locked orientation, such that set screw 202 fixes rod 200 with connector 12.

Body 16 includes a mating surface, such as, for example, a splined surface 30. Splined surface 30 is configured for a splined connection 32 with a mating surface, such as, for example, a splined surface 134 of a washer 128, which is connected to or part of receiver 114, as described herein. Splined connection 32 is configured to facilitate incremental and selective positioning of a spinal implant, such as, for example, a spinal rod 204 relative to an existing spinal construct, including spinal rod 200, via relative movement of the respective spline surfaces 30, 134, and locking of spinal rod 204 relative to the existing spinal construct via mesh engagement of the respective spline surfaces. Splined connection 32 is moveable between a non-locked and a locked configuration, via compression of an O-ring 136, as described herein, to selectively rotate spinal rod 204 to a selected position relative to the existing spinal construct and/or tissue, as described herein.

Figure 9:
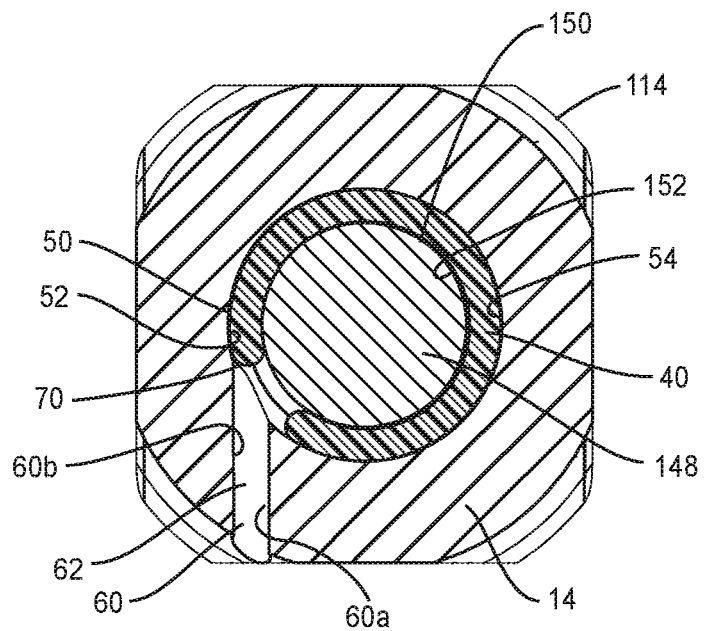
FIG. 9 is a cross section view of components of the system taken along the lines A-A of FIG. 8.

Receiver 14 is connected with receiver 114 by a flexible element, such as, for example, a wire 40, as described herein. Wire 40 is configured for disposal with a passageway, such as, for example, an assembly channel 54 formed by alignment of receivers 14, 114, as described herein, to connect receivers 14, 114. Body 16 includes a surface 50 that defines a cavity 51. Cavity 51 is configured to receive a portion of body 116, as described herein, to facilitate assembly of connector 12. Surface 50 includes an outer circumferential surface 52 of channel 54, as shown in FIG. 9. Surface 150 includes an inner circumferential surface 152 of channel 54, as shown in FIG. 9. Surface 52 is disposable in communication and alignment with surface 152 to form channel 54.

Body 16 includes a surface 60 that defines an opening 62. Opening 62 is disposed in communication with channel 54 such that wire 40 is inserted through opening 62 into channel 54 for assembly of connector 12. Opening 62 extends transverse to channel 54, as shown in FIG. 9, such that opening 62 intersects with channel 54. In some embodiments, a portion 60a of surface 60 is tangentially aligned with surface 152 and a portion 60b of surface 60 is offset and not tangentially aligned with surface 52 adjacent the intersection of opening 62 with channel 54. As such, surface 60b connects with surface 52 to form a projection 70. Projection 70 extends a distance into channel 54 to resist and/or prevent wire 40 from backing out from channel 54. In some embodiments, this configuration eliminates additional assembly steps, for example, staking, for maintaining wire 40 in passageway 54. In some embodiments, opening 62 extends perpendicular and/or other angular orientations such as acute or obtuse, coaxial and/or may be offset or staggered relative to surface 52.

Figure 5:
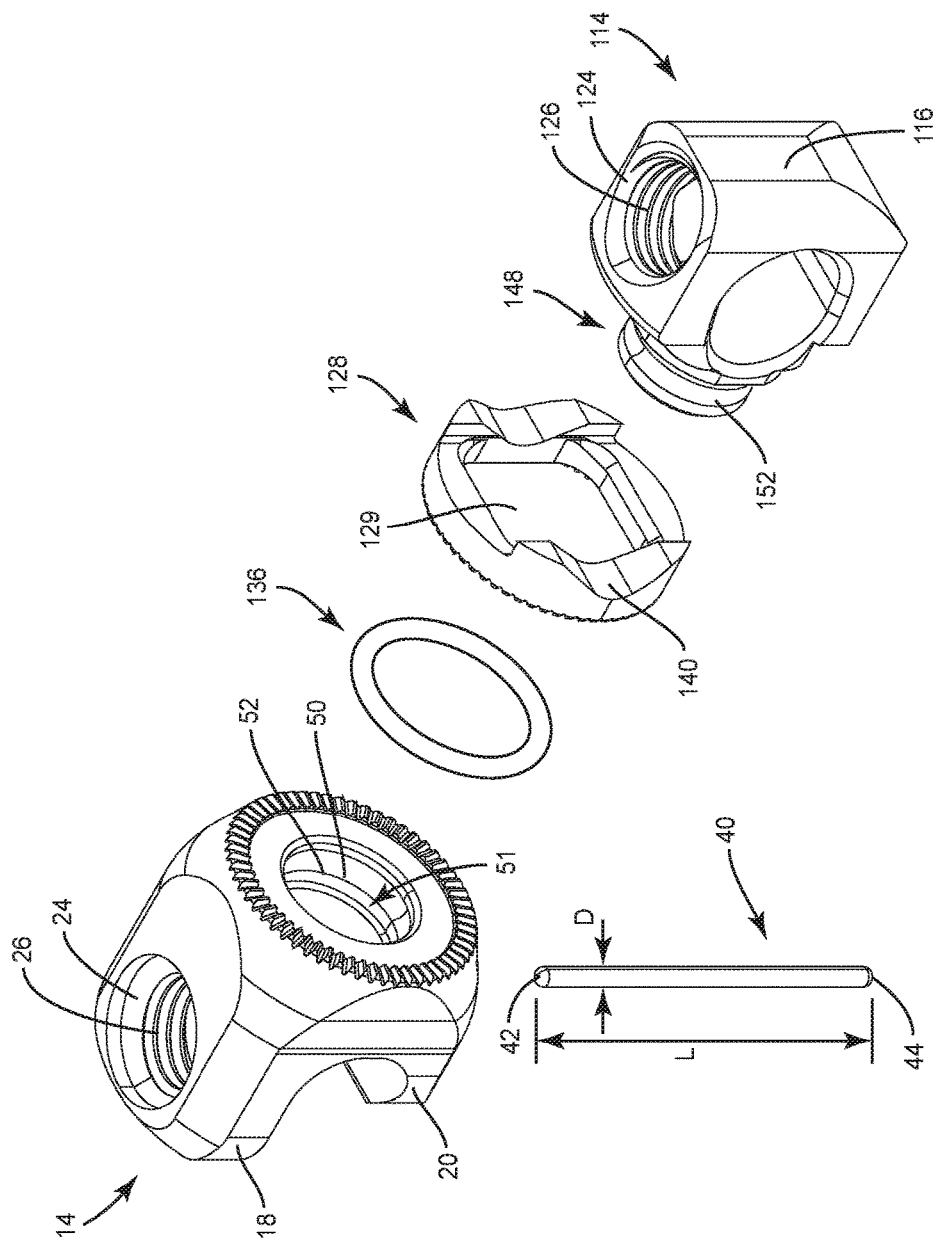
FIG. 5 is a perspective exploded view of components of one embodiment of a system in accordance with the principles of the present disclosure.

Wire 40 extends between an end 42 and an end 44, as shown in FIG. 5. Wire 40 is configured for disposal with channel 54, as described herein, to facilitate connection of receivers 14, 114. Wire 40 includes a length L and a diameter D. Wire 40 is configured to connect receiver 14 with receiver 114 while allowing for relative rotation of receiver 14 and receiver 114 for selective positioning of spinal rods 200, 204. Length L and diameter D are selected to facilitate rotation between receiver 14 and receiver 114.

Figure 10:
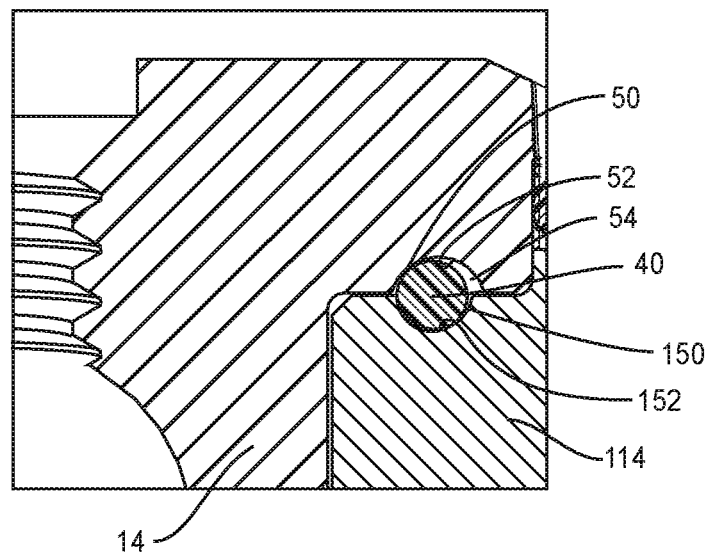
FIG. 10 is a cross section view of components of the system taken along the lines B-B of FIG. 8.

Length L of wire 40 is selected so that when wire 40 is driven or translated through opening 62 of connector 14 and then into channel 54, wire 40 creates a C-shape, as shown in FIG. 9. Diameter D of wire 40 is selected such that wire 40 is movable and/or does not occupy the entire space and/or diameter of channel 54, as shown in FIGS. 9 and 10. Wire 40 is biased within channel 54 to expand outwardly such that wire 40 contacts surface 52. In some embodiments, wire 40 is expandable within channel 54 and contacts only surface 52. In some embodiments, wire 40 is expandable within channel 54 and contacts surface 52 and/or surface 152. For example, providing movement of diameter D in channel 54 and/or providing space between surfaces 52, 152 of channel 54 and diameter D decreases friction between wire 40 and surfaces 52, 152 to facilitate slidable rotation between receivers 14, 114. In some embodiments, this configuration of wire 40 and channel 54 limits tolerance and/or toggle between receivers 14, 114, and resists receivers 14, 114 from moving apart while allowing receivers 14, 114 to relatively rotate about a common axis.

In some embodiments, all or only a portion of wire 40 may have flexible properties, such as the flexible properties corresponding to the material examples described above, such that wire 40 provides a selective amount of expansion and/or extension in an axial direction. In some embodiments, all or only a portion of wire 40 may have a semi-rigid, rigid or elastic configuration, and/or have elastic properties, such as the elastic properties corresponding to the material examples described above, such that wire 40 provides a selective amount of expansion and/or extension in an axial direction. The flexible element, whether a wire 40, is in some embodiments a spring, having a generally straight state, in which it is installed through opening 62. Upon being forced to a bent state by outer surface 52 of channel 54, spring action of the element pushes outward against outer surface 52 as the element tries to return to the straighter state.

In some embodiments, wire 40 has a flexible configuration, which includes movement in a lateral or side to side direction. In some embodiments, wire 40 may be compressible in an axial direction. Wire 40 can include a plurality of separately attachable or connectable portions or sections, such as bands or loops, or may be monolithically formed as a single continuous element.

Wire 40 can have a uniform thickness/diameter. In some embodiments, wire 40 may have various surface configurations, such as, for example, rough, threaded for connection with surgical instruments, arcuate, undulating, porous, semi-porous, dimpled, polished and/or textured. In some embodiments, the thickness defined by wire 40 may be uniformly increasing or decreasing, or have alternate diameter dimensions along its length. In some embodiments, wire 40 may have various cross section configurations, such as, for example, oval, oblong, triangular, rectangular, square, polygonal, irregular, uniform, non-uniform, variable and/or tapered. In some embodiments, wire 40 may have various lengths. In some embodiments, wire 40 may be braided, such as a rope, or include a plurality elongated elements to provide a predetermined force resistance. In some embodiments, wire 40 can be deformable, malleable or plastically deformable.

Receiver 114 includes a body 116, which defines a wall 118. Wall 118 includes a surface 120 that defines a closed implant cavity, such as, for example, a passageway 122. Passageway 122 is configured for disposal of spinal rod 204 to extend and/or revise an existing spinal construct, as described herein. Passageway 122 is configured for front loading of spinal rod 204 along an axis X2. In some embodiments, passageway 122 can be positioned for alternate loading orientations, such as, for example, top, side and/or lateral.

Figure 4:
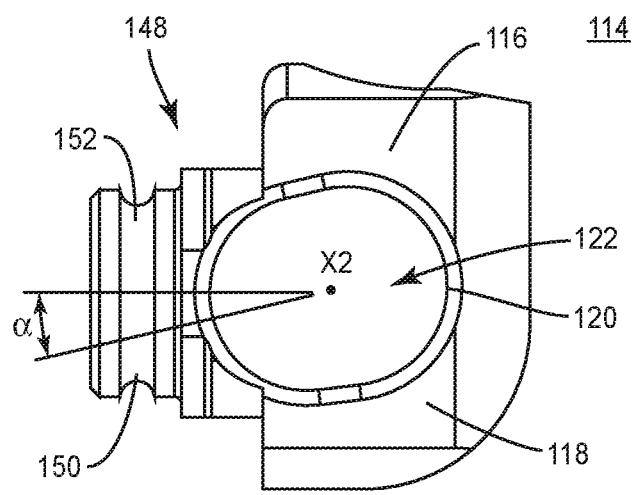

Passageway 122 is in various embodiments substantially oval or tear drop shaped, as shown in FIG. 4. Passageway 122 in various embodiments includes a floor 123 (see FIG. 11) declining towards washer 128. In various embodiments, passageway 122, including floor 123 and a roof opposite, declines, or has an angled cross section declining toward washer 128, as described herein. In some embodiments, floor and/or the angled cross section, includes a downward-sloped and/or angled portion defining an angle α, as shown in FIG. 4, to facilitate pushing of spinal rod 204 towards washer 128, including when force being applied to spinal rod 204 via a set screw 206 (see e.g. FIGS. 13, 16 and 18). In some embodiments, this configuration creates a larger opening for insertion of spinal rod 204. In some embodiments, this configuration includes an angle and positioning of set screw 206 relative to a lateral half of spinal rod 204 to facilitate driving, guiding and/or directing spinal rod 204 towards washer 128 to lock receivers 14, 114 in a selected in position, as described herein. In some embodiments, set screw 206 is disposed at an angle β relative to an axis X3 of receiver 114, as shown in FIG. 13. In some embodiments, set screw 206 may include a dimpled or angled tip to facilitate set screw 206 engagement with spinal rod 204, and pushing spinal rod 204 towards washer 128.

In some embodiments, all or only a portion of passageway 122 may have alternate cross section configurations, such as, for example, circular, U-shaped, V-shaped, W-shaped, oblong triangular, square, polygonal, irregular, uniform, non-uniform, offset, staggered, and/or tapered.

Body 116 includes an inner surface 124. A portion of surface 124 includes a thread form 126. Thread form 126 is configured for engagement with a coupling member, such as, for example, a set screw 206, to retain rod 204 within passageway 122, as shown in FIG. 13. In some embodiments, surface 124 may be disposed with set screw 206 in alternate fixation configurations, such as, for example, friction fit, pressure fit, locking protrusion/recess, locking keyway and/or adhesive. In some embodiments, all or only a portion of surface 126 may have alternate surface configurations to enhance engagement with spinal rod 204 and/or set screw 206 such as, for example, rough, arcuate, undulating, mesh, porous, semi-porous, dimpled and/or textured. Set screw 206 is configured for engagement with rod 204 to facilitate fixation and/or locking of spinal rod 204 with receiver 114. Set screw 206 is disposable with receiver 114 between a non-locking orientation, such that spinal rod 204 is translatable relative to connector 12 and a locked orientation, such that the set screw fixes rod 204 with connector 12.

Body 116 is connectable with a washer 128. Washer 128 includes a circular configuration. Washer 128 includes an opening 129. Opening 129 is configured for disposal of a post 148 of body 116 such that insertion of spinal rod 204 actuates translation of washer 128 for locking receiver 114 with receiver 14, as described herein.

Figure 6:
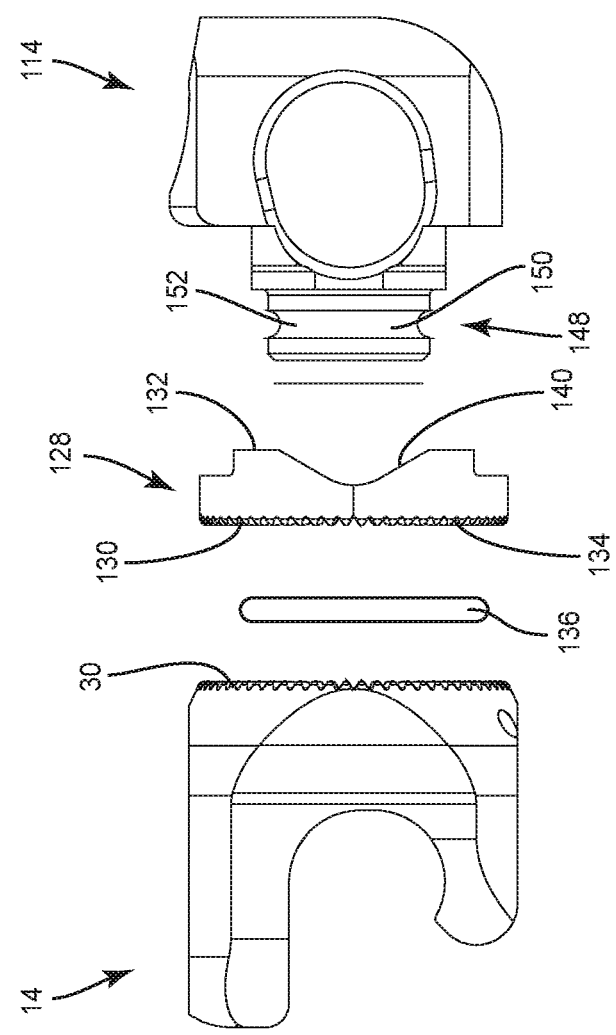
FIG. 6 is a side exploded view of components of one embodiment of a system in accordance with the principles of the present disclosure.

Washer 128 extends between an end 130 and an end 132, as shown in FIG. 6. End 130 includes splined surface 134. Splined surface 134 is configured for splined connection 32 with splined surface 30, as described herein. A biasing element, such as, for example, an O-ring 136 is disposed between surface 134 and surface 30. O-ring 136 is configured to apply a force to surfaces 134, 30 to bias surfaces 134, 30 in a spaced apart relation to maintain surfaces 134, 30 in the non-locking orientation to facilitate relative rotation of receivers 14, 114.

End 132 includes a surface 140. In some embodiments, surface 140 is arcuate to facilitate engagement with spinal rod 204. For example, upon fixation of spinal rod 204 with receiver 114, as described herein and shown in FIG. 13, spinal rod 204 applies a force to surface 140. The force applied to surface 140 by spinal rod 204 causes washer 128 to translate, in a direction shown by arrow A in FIG. 13. Translation of washer 128 causes surface 134 to compress O-ring 136 and overcome the biasing force of O-ring 136. Translation of surface 134 causes surface 134 to interlock with surface 30 into splined connection 32 to fix the selected positions of spinal rod 204 and spinal rod 202.

Figure 7:
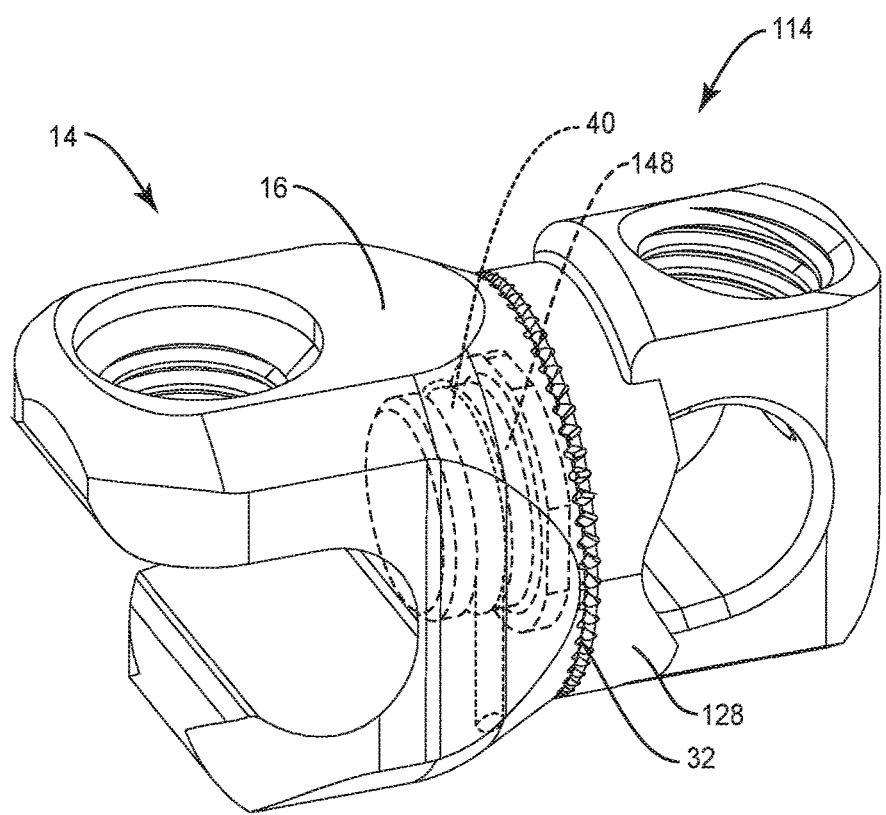
FIG. 7 is a first perspective view in cutaway phantom of components of one embodiment of a system in accordance with the principles of the present disclosure.
Figure 8:
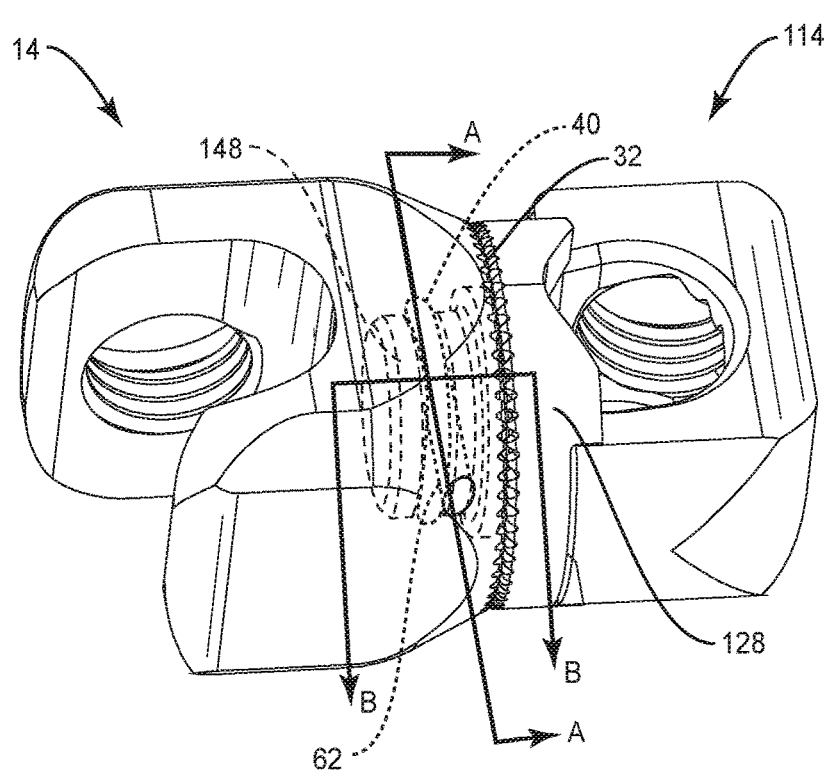
FIG. 8 is a second perspective view in cutaway phantom of components of one embodiment of a system in accordance with the principles of the present disclosure.
Figure 11:
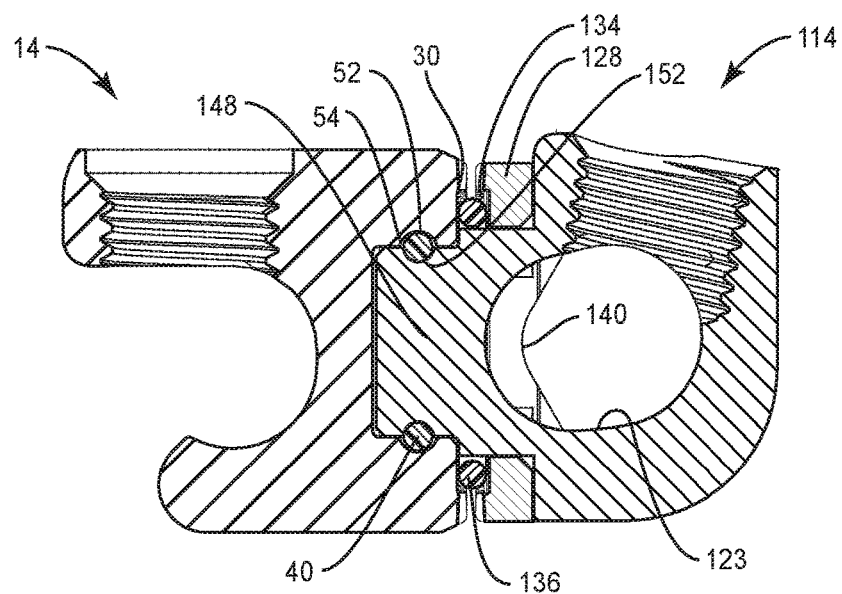
FIG. 11 is a side cross section view of components of one embodiment of a system in accordance with the principles of the present disclosure.
Figure 12:
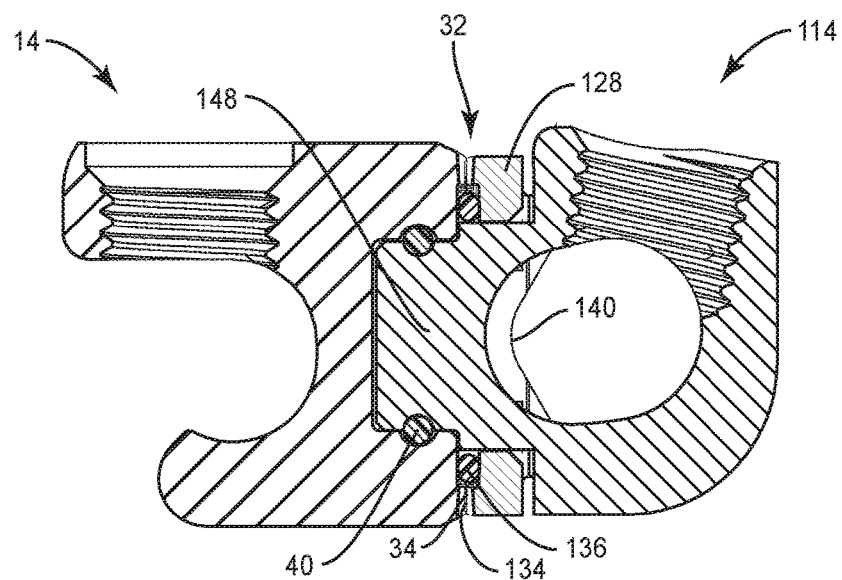
FIG. 12 is a side cross section view of the components shown in FIG. 11.

Post 148 is configured for disposal with opening 129 of washer 128, as shown in FIG. 6. Post 148 is configured for disposal with cavity 51 of body 16, as shown in FIGS. 5 and 7. Post 148 includes surface 152 disposed circumferentially about post 148. Surfaces 52, 152 are aligned to form channel 54, as described herein. For example, body 116 is assembled with body 16 such that post 148 is disposed with cavity 51. Positioning of post 148 with cavity 51 aligns surfaces 52, 152 to form channel 54. Wire 40 is inserted into opening 62 and translated into channel 54 such that wire 40 is circumferentially disposed about post 148, as shown in FIG. 9. Wire 40 is expandable and resilient between a contracted orientation for insertion and an expanded orientation for relative fixation of receivers 14, 114. Upon insertion of wire 40, wire 40 expands outwardly, as described herein and shown in FIG. 10. Wire 40 connects receiver 114 with receiver 14 for assembly of connector 12, as shown in FIGS. 11 and 12.

In some embodiments, spinal implant system 10 can include one or a plurality of connectors 12 such as those described herein, which may be employed with a single vertebral level or a plurality of vertebral levels. In some embodiments, one or more connectors 12 may be engaged with vertebrae in various orientations, such as, for example, series, parallel, offset, staggered and/or alternate vertebral levels. In some embodiments, one or more connectors 12 may be employed with multi-axial screws, sagittal angulation screws, pedicle screws, mono-axial screws, uni-planar screws, fixed screws, anchors, hooks, tissue penetrating screws, conventional screws, expanding screws, wedges, anchors, buttons, clips, snaps, friction fittings, compressive fittings, expanding rivets, staples, nails, adhesives, posts, connectors, fixation plates and/or posts.

In assembly, operation and use, spinal implant system 10, similar to the systems and methods described herein, is employed with a surgical procedure, such as, for example, a surgical treatment of an applicable condition or injury of an affected section of a spinal column and adjacent areas within a body. In some embodiments, spinal implant system 10 includes connector 12, as described herein, which is attached with vertebral tissue being treated. In some embodiments, spinal implant system 10 includes connector 12, as described herein, which can be employed in a surgical treatment such as a revision surgery to strengthen, revise, repair and/or extend an existing spinal construct. In some embodiments, spinal implant system 10 includes connector 12 employed in a revision surgery to connect with an existing spinal construct and strengthen the existing spinal construct to span one or more spinal levels. In some embodiments, the existing spinal construct may include one or more implants connected or fixed with tissue in a prior or different surgical procedure, separate in time and/or over a duration of time in the same surgical procedure. In some embodiments, during a surgical treatment, spinal implant system 10 may be completely or partially revised, removed or replaced.

Figure 14:
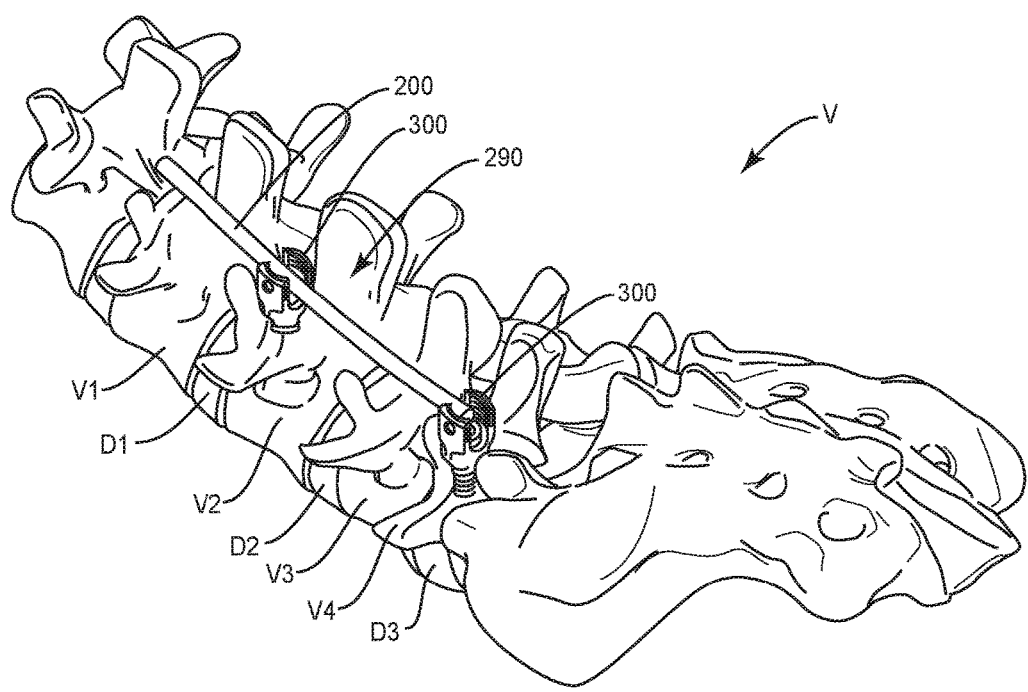
FIG. 14 is a perspective view of components of one embodiment of a system, disposed with vertebrae, in accordance with the principles of the present disclosure.
Figure 15:
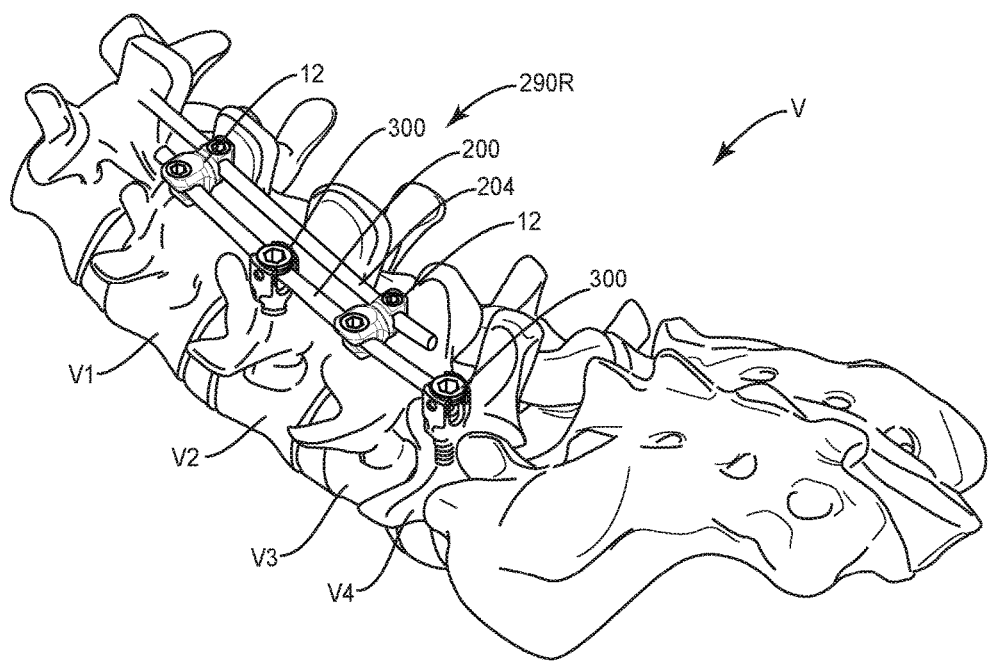
FIG. 15 is a perspective view of components of one embodiment of a system, disposed with vertebrae, in accordance with the principles of the present disclosure.

For example, a surgical treatment may include adding strength and support to an existing spinal construct 290 that includes fastener 300 and existing spinal rod implant 200, as shown in FIG. 14, implanted with vertebrae V in a prior surgical procedure and spans one or more intervertebral discs. In the prior surgical procedure, existing spinal rod implant 200 is implanted to structurally fuse adjacent vertebrae V1, V2, V3, V4 with existing spinal construct 290, which includes fasteners 300 and existing spinal rod implant 200, to span intervertebral discs D1, D2, D3. In one example, the surgical procedure requires utilization of multiple rods, such as, for example, existing spinal rod implant 200 and rod 204, as shown in FIG. 15.

In some embodiments, multiple rods are required for a high load demand, such as, for example, a pedicle subtraction osteotomy, a lumbar fixation, a heavier patient and/or a revision surgery subsequent or different to the prior surgical procedure. In some embodiments, the treatment includes connector 12 employed in a revision surgery to connect with spinal rod 200 to form a revised spinal construct 290R that strengthens spinal construct 290 along spinal levels V1-V4, as described herein. In some embodiments, this configuration avoids disruption and tissue damage of the area of the prior surgical procedure, and reduction in healing and treatment duration.

In connection with the surgical procedure, to treat a selected section of vertebrae V, including vertebrae V1, V2, V3, V4, a medical practitioner obtains access to a surgical site including vertebrae V in any appropriate manner, such as through incision and retraction of tissues. In some embodiments, spinal implant system 10 can be used in any surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway to access an existing spinal construct 290 including implanted fastener 300 and implanted existing spinal rod implant 200. The surgical pathway is utilized for implantation of components of spinal implant system 10. A preparation instrument (not shown) can be employed to prepare tissue surfaces of vertebrae V, as well as for aspiration and irrigation of a surgical region.

Connector 12 is assembled, as described herein, prior to the surgical procedure, for example, during manufacturing of components of spinal implant system 10, or in the operating room or in situ. Connector 12 is disposed adjacent the existing spinal construct 290 for engagement with spinal rod 200. Spinal rod 200 is disposed with passageway 22. Spinal rod 200 is fixed with receiver 14 via set screw 202. Set screw 202 is engaged with a surgical instrument, such as, for example, a driver (not shown), which advances set screw 202 into engagement with thread form 26 of receiver 14 for disposal in a locking orientation with spinal rod 200, as described herein. In some embodiments, a driver can engage set screw 202 to provisionally fix spinal rod 200 with receiver 14 to facilitate disposal of spinal rod 204 with receiver 114.

Spinal rod 204 is delivered along the surgical pathway and is disposed with passageway 122. In some embodiments, spinal rods 200, 204 are selectively manipulated and/or contoured for the surgical treatment and/or to accommodate anatomical differences. O-ring 136 maintains surfaces 30, 134 in the non-locked orientation such that receivers 14, 114 relatively and/or independently rotate to facilitate positioning of spinal rods 200, 204 with the components of spinal construct 290. With spinal rod 200 disposed with receiver 14, receivers 14, 114 can be relatively and/or independently rotated and/or spinal rod 200 can be moved relative to connector 12, for disposing spinal rod 204 with receiver 114. Spinal rod 204 is fixed with receiver 114 via set screw 206. Set screw 206 is engaged with a surgical instrument, such as, for example, a driver (not shown), which advances set screw 206 into engagement with thread form 126 of receiver 114 in a locking orientation, as described herein. The driver engages set screw 206 to fix spinal rod 204 with receiver 114 and for attachment of spinal rod 204 with vertebrae V.

As set screw 206 advances into engagement with spinal rod 204, spinal rod 204 applies a force to surface 140. The force applied to surface 140 by spinal rod 204 causes washer 128 to translate, in a direction shown by arrow A in FIG. 13. O-ring 136 is compressed by washer 128 overcoming the biasing force of O-ring 136. Surface 134 interlocks with surface 30 into splined connection 32 to fix the relative orientation of receivers 14, 114 and the selected positions of spinal rods 204, 200.

Connector 12 and spinal rod 204 are manipulated to dispose spinal rod 204 in a position to support and strengthen the existing spinal construct, which included spinal rod 200, to form a revised spinal construct 290R. Revised spinal construct 290R strengthens existing spinal construct 290 along vertebrae V1-V4 without disruption of existing spinal construct 290. Spinal construct 290R is configured to structurally fuse adjacent vertebrae V1-V4. In some embodiments, spinal rod 204 is configured to add support and strength to spinal implant system 10 along vertebrae V. In some embodiments, spinal construct 290R is adjustable to selectively span one or more vertebrae.

Figure 16:
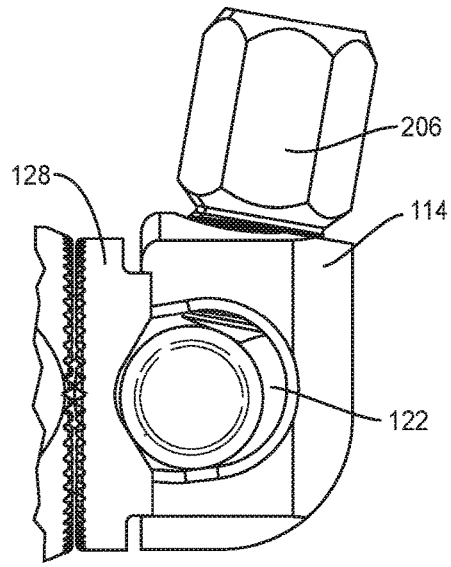
FIG. 16 is a side view of components of one embodiment of a system in accordance with the principles of the present disclosure.
Figure 18:
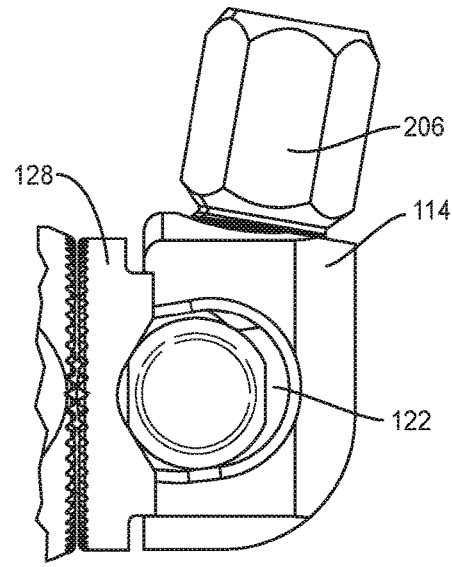
FIG. 18 is a side view of components of one embodiment of a system in accordance with the principles of the present disclosure.
Figure 17:
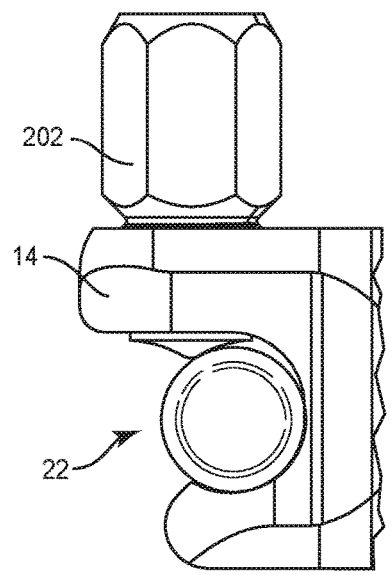
FIG. 17 is a side view of components of one embodiment of a system in accordance with the principles of the present disclosure.
Figure 19:
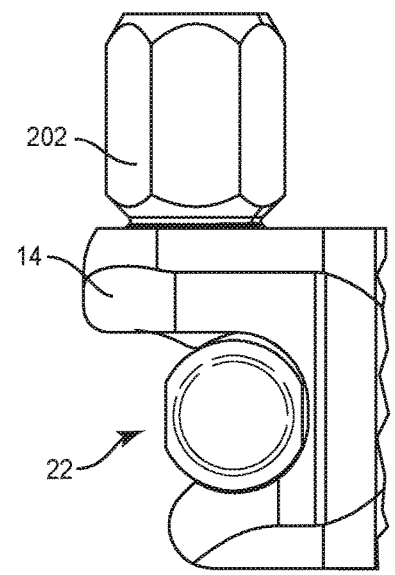
FIG. 19 is a side view of components of one embodiment of a system in accordance with the principles of the present disclosure.

In some embodiments, receivers 14, 114 are configured to accommodate a range of spinal rods. In some embodiments, receivers 14, 114 are configured to accommodate spinal rods having a diameter of 5.5 mm, as shown in FIG. 13. In some embodiments, receivers 14, 114 are configured to accommodate spinal rods having a diameter of 6.0 mm, as shown in FIGS. 16 and 17. In some embodiments, receivers 14, 114 are configured to accommodate spinal rods having a diameter of 6.3 mm, as shown in FIGS. 18 and 19. In some embodiments, receivers 14, 114 are configured to accommodate spinal rods having a diameters in a range of 5.5 mm of 6.3 mm. In some embodiments, receivers 14, 114 are configured to accommodate spinal rods having various cross sections, such as, for example, shaped, oval, oblong triangular, square, polygonal, irregular, uniform, non-uniform, offset, staggered, and/or tapered. In some embodiments, the dimensions of set screw 206 are configured to accommodate various sized spinal rods. For example, a smaller spinal rod provides for leaving more thread above the spinal rod after locking the spinal rod. In some embodiments, a larger spinal rod provides for leaving less thread above the spinal rod. As such, set screw 206 is configured appropriately to push enough against the spinal rod to facilitate engagement for stability after full insertion of set screw 206.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, robotics, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A connector comprising:
   a first receiver defining an implant cavity and including a mating surface, an inner surface, and an outer surface opposite the inner surface, the inner surface defining a first portion of a passageway, the first receiver defining an opening extending through the outer surface such that the opening is in communication with the passageway;

a second receiver defining a second portion of the passageway, a first part being inserted through the opening and into the passageway to attach the second receiver with the first receiver, the second receiver defining an implant cavity and including a mating surface engageable with the mating surface of the first receiver to fix relative orientation of the receivers; and a second part disposed adjacent the mating surfaces to space the mating surfaces such that the first receiver is movable relative to the second receiver in operation of the connector.

2. A connector as recited in claim 1, wherein the implant cavity of the first receiver is configured for disposal of a first spinal rod and the implant cavity of the second receiver is configured for disposal of a second spinal rod.

3. A connector as recited in claim 1, wherein the receivers are disposable between a non-locked orientation such that the second part spaces apart the mating surfaces and a locked orientation such that mating surfaces are fixed, relative to each other, to selectively orient the first receiver relative to the second receiver.

4. A connector as recited in claim 1, wherein the second part includes a flexible O-ring.

5. A connector as recited in claim 1, wherein the mating surfaces include splines.

6. A connector as recited in claim 1, wherein the mating surface of the second receiver includes a splined surface of a washer disposed with the second receiver.

7. A connector as recited in claim 6, wherein the washer is movable relative to the second receiver to engage the splined surface with a splined surface of the first receiver.

8. A connector as recited in claim 1, wherein the first part is expandable in the passageway.

9. A connector as recited in claim 1, wherein the first part is configured to bias outwardly to expand in the passageway.

10. A connector as recited in claim 1, wherein the opening extends transverse to the passageway.

11. A connector as recited in claim 1, wherein the outer surface of the first receiver is an outer circumferential surface and the second receiver includes an inner circumferential surface defining the second portion of the passageway.

12. A connector as recited in claim 11, wherein the outer circumferential surface includes a projection to resist and/or prevent back out of the first part from the passageway.

13. A connector as recited in claim 1, wherein the second receiver includes a post having an inner circumferential surface, the inner circumferential surface defining the second portion of the passageway, the implant cavity of the second receiver being disposed at an acute angle relative to the post.

14. A connector as recited in claim 1, wherein a floor of the second receiver is sloped towards a washer of the second receiver to drive a second spinal rod into engagement with the washer.

15. A connector as recited in claim 1, wherein the first part is a wire.

16. A connector as recited in claim 1, wherein the first part is inserted through the opening with the first part in a straight state, the first part moving from the straight state to a bent state when the first part is positioned within the passageway.

17. A connector as recited in claim 1, wherein the second receiver includes a first end including a post and a second end opposite the first end, the first and second ends each extending from a first side wall to a second side wall, the implant cavity of the second receiver extending through the side walls, the second receiver comprising opposite top and bottom walls each extending from the first end to the second end and from the first side wall to the second wall, the second receiver defining a threaded opening extending through the top wall, the bottom wall being free of any openings.

18. A connector comprising:

a first receiver defining an implant cavity and including an inner surface and an outer surface opposite the inner surface, the inner surface defining a first portion of a passageway, the first receiver defining an opening extending through the outer surface such that the opening is in communication with the passageway;

a second receiver defining a second portion of the passageway and an implant cavity; and a wire inserted through the opening and into the passageway to attach the second receiver with the first receiver.

19. A connector as recited in claim 18, wherein the wire is inserted through the opening with the wire in a straight state, the wire moving from the straight state to a bent state when the wire is positioned within the passageway.

20. A connector comprising:

a first receiver defining an implant cavity and including a mating surface;

a second receiver attachable with the first receiver via a first part, the second receiver defining an implant cavity and including a mating surface engageable with the mating surface of the first receiver to fix relative orientation of the receivers; and a second part disposed adjacent the mating surfaces to space the mating surfaces such that the first receiver is movable relative to the second receiver in operation of the connector, wherein the receivers are connected to define a passageway for disposal of the first part, wherein the first receiver includes an outer circumferential surface and the second receiver includes an inner circumferential surface, the surfaces defining the passageway, and wherein the outer circumferential surface includes a projection to resist and/or prevent back out of the first part from the passageway.

* * * * *